(12) United States Patent
Ludvig et al.

(10) Patent No.: US 6,602,220 B1
(45) Date of Patent: Aug. 5, 2003

(54) MINIATURE AIR-CONTROLLED DRUG SELECTOR AND DELIVERY DEVICE PORTABLE BY SMALL ANIMALS

(75) Inventors: Nandor Ludvig, Forest Hills, NY (US); Geza Medveczky, Bedford Hills, NY (US); Lorant Kovacs, Mt. Kisco, NY (US); Laszlo Kando, Hopewell Junction, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/579,199

(22) Filed: May 26, 2000

(51) Int. Cl.$^7$ .................................. A61M 1/00
(52) U.S. Cl. ........................................... 604/30
(58) Field of Search .................... 604/30, 31, 32, 604/33, 34, 29, 28, 65, 236, 246, 254

(56) References Cited

U.S. PATENT DOCUMENTS

| | | | |
|---|---|---|---|
| 4,807,170 A | * 2/1989 | Kulli et al. | 604/30 |
| 5,549,569 A | * 8/1996 | Lynn et al. | 600/573 |
| 5,743,886 A | * 4/1998 | Lynn et al. | 604/191 |
| 5,816,256 A | 10/1998 | Kissinger et al. | |
| 5,832,878 A | 11/1998 | Bonsall et al. | |
| 5,865,766 A | 2/1999 | Bonsall et al. | |
| 6,110,139 A | * 8/2000 | Loubser | 604/30 |

\* cited by examiner

*Primary Examiner*—Daniel Robinson
(74) *Attorney, Agent, or Firm*—Scully, Scott, Murphy & Presser

(57) ABSTRACT

A minivalve for delivering one of a control solution or a drug solution to a point of interest in a freely moving animal. The minivalve is portable by the freely moving animal, such as a mouse, rat, or primate, on its head without interfering with its behavior. The minivalve having an input for a control solution and an input for a drug solution and further having a common output for outputting either of the control solution or drug solution to an input of a microdialysis probe implanted at a point of interest in the animal. Also provided are systems for delivering one of a control solution or a drug solution to a point of interest in the animal. The system comprises the minivalve, a drug ejection device such as a microdialysis probe or injection cannula implanted at the point of interest in the small animal, and a microelectrode placed adjacent to the drug ejection device. The minivalve is designed to be easily modified to be actuated with a gas or liquid, to be used in larger animals and in humans, to be mounted on body parts other than the head, to be used for drug delivery into other body organs than the brain, and to be integrated into various industrial/scientific instruments.

4 Claims, 10 Drawing Sheets

First ethanol perfusion

Second ethanol perfusion 60 min later

NMDA perfusion 2 hours after second ethanol

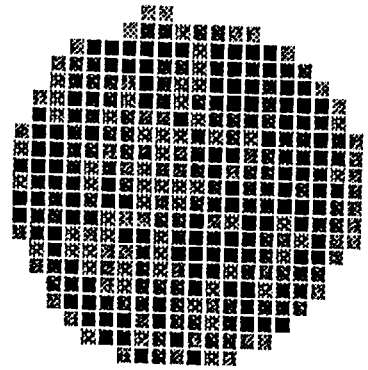
FIG.9b Staying Time Distribution map — minivalve installed
0.50 0.99 1.43 1.99 2.84 7.42 sec
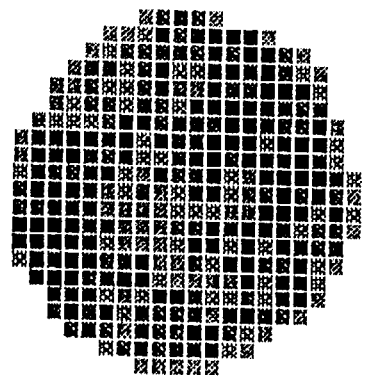
FIG.9a Staying Time Distribution map — minivalve not installed
0.34 0.99 1.52 2.14 2.95 6.96 sec

MINIATURE AIR-CONTROLLED DRUG SELECTOR AND DELIVERY DEVICE PORTABLE BY SMALL ANIMALS

GOVERNMENT LICENSE RIGHTS

The U.S. Government has a paid-up license in this invention and the right in limited circumstances to require the patent owner to license others on reasonable terms as provided for by the terms of Grant No. R41 MH56800 awarded by the National Institute for Health.

BACKGROUND OF THE INVENTION

1. Field of the Invention

The present invention relates generally to remote-controlled drug deliveries into the body of animals or humans, and more particularly, to a miniature, lightweight, air-controlled minivalve portable by small laboratory animals on their head without affecting their behavior.

2. Prior Art

Drug delivery into the brain of experimental animals is a commonly used method in the academia and the pharmaceutical industry to characterize the neurobiological effects of various chemical compounds. Microdialysis is one method to deliver drugs into the brain. This procedure utilizes a microdialysis fiber implanted into a point of interest in the brain and connected to an inlet and an outlet tube. Through the inlet tube, either a control or a drug solutions is driven into the microdialysis fiber, allowing the diffusion of the drugs into the surrounding tissue, which, in turn, induces various neurobiological effects. Through the outlet tube, the control or drug solution leaves the microdialysis fiber and the point of interest in the brain.

To alternate the flow of control and drug solutions in the implanted microdialysis probe liquid switches and valves have been used. These liquid switches are large and heavy, and are therefore placed far from the animal. Because of this, with their use it takes a long time, often an hour, for the control or drug solution to reach the animal and the implanted microdialysis probe. This lengthens the experiments unnecessarily, obscures the onset and offset of the drug effects, and makes it impossible to deliver the drugs when a specific behavioral event occurs. There are various solenoid valves available, which are smaller and lighter than the valves and liquid switches. However, the available solenoid valves are unable to continuously receive a control and a drug solution, to select between these two solutions, and to direct one of them into the microdialysis probe and one of them into a waste line. As a consequence, they cannot be used for delivering drugs via the microdialysis procedure.

Various minipumps, such as osmotic or Esox pumps, are also available for drug deliveries into the body. The disadvantage of these pumps are two-fold. First, they are able to deliver only one or a maximum of two drug solutions without repositioning or refilling them in the body. As a consequence, the behavior of the subject is disturbed, confounding the obtained data and complicating the experiment. Second, these minipumps are capable of only delivering drugs and not to simultaneously extract fluids from the brain, which is readily offered by microdialysis. As a consequence, only a fraction of the neurobiological effects of the drug-effects can be detected using minipumps of the prior art.

Because of the above limitations of commercially available valves, liquid switches, solenoid valves, and minipumps, drug deliveries into the brain of experimental animals have been time-consuming, unreliable and limited in terms of extracting information from the brain. A miniature, light-weight, remotely-controlled valve is needed, which is portable by the laboratory animal on its head without interfering with its behavior, allowing the alternation of the control and drug solutions close to the brain and driving the selected solution into a microdialysis probe. This would allow the rapid delivery of drugs through the implanted microdialysis probe and the instantaneous detection of the drug-induced neurobiological effects. As a consequence, the experiments would not be time-consuming, the onset and offset of drug effects would not be obscure, and multiple drug deliveries during the occurrence of special behavioral events would be possible without affecting the subject's behavior. Optimally, the use of such a miniature, light-weight, remotely controlled valve should be extended to the use in experiments with all types of animals, to use in humans in clinical practice, and to use in various industrial/scientific instruments. For purposes of this disclosure, the term animals includes humans.

SUMMARY OF THE INVENTION

Therefore, it is an object of the present invention to provide a minivalve for rapidly delivering drugs into the brain of freely moving animals, including small animals and primates, via a microdialysis probe connected to the minivalve and implanted into the brain of the animals.

It is a further object of the present invention to provide a system for effectively using the minivalve to rapidly deliver many drugs into the brain and to detect the drug-induced neurobiological changes instantly.

The present invention eliminates the difficulties associated with the use of traditional valves, liquid switches and solenoid valves. The invention is a miniature, light-weight, remotely-controlled valve, referred hereinafter as "minivalve", which is portable by small laboratory animals on their head without interfering with their behavior. The minivalve of the present invention allows rapid drug delivery into the brain of freely moving small animals, such as mice or rats, through a microdialysis probe, and to detect the neurobiological effects of the delivered drugs instantly.

The method for delivering drugs into the brain of small animals with the use of the minivalve of the present invention comprises; the implantation of a microdialysis probe and a microelectrode into the brain of small animals, the mounting of the minivalve on the head of the small animal, and detecting the effects of drugs delivered through the microdialysis probe.

Accordingly, a minivalve for delivering one of a control solution or a drug solution to a point of interest in a small animal is provided. The minivalve has an input for a control solution and an input for a drug solution and a common output for outputting either of the control solution or drug solution to an input of a microdialysis probe implanted at a point of interest in the small animal. The minivalve further having actuation means for actuating the minivalve between first and second positions in which the control solution or drug solution is selectively input to the microdialysis probe.

Preferably, the actuation means for actuating the minivalve between first and second positions comprises a fluid switch slidably disposed within a housing. The fluid switch is preferably actuated between the first and second positions by a differential in gas pressure between first and second gas inputs, a greater gas pressure at the first gas input actuating the fluid switch into the first position and a greater gas pressure at the second gas input actuating the fluid switch into the second position. The minivalve is preferably actuated by gas, and most preferably by air. However, the actuation can be produced with a liquid instead of gas.

Also provided is a system for delivering one of a control solution or a drug solution to a point of interest in a small animal. The system comprises: a microdialysis probe implanted at the point of interest in the small animal, the microdialysis probe allowing the diffusion of the drug solution across a membrane and into the point of interest, the microdialysis probe having an input for acceptance of one of the control or drug solutions therein and an output for outputting a dialysate therefrom; a minivalve mounted on the small animal, the minivalve having an input for the control solution and an input for the drug solution, the minivalve further having a common output for outputting either of the control solution or drug solution to the input of the microdialysis probe, the minivalve further having actuation means for actuating the minivalve between first and second positions in which the control solution or drug solution is selectively input to the microdialysis probe; and a microelectrode placed adjacent to the implanted microdialysis probe to allow the detection of the effects of the delivered drugs.

Preferably the small animal is a rat, mouse, monkey or other small animal, the minivalve is mounted on the head of the small animal, and the point of interest for implantation of the microdialysis probe is in the brain of the small animal.

Still yet provided is a method for delivering one of a control solution or a drug solution to a point of interest in a small animal. The method comprises the steps of: implanting a microdialysis probe and a microelectrode at a point of interest in the small animal; mounting a minivalve on the small animal, the minivalve having an input for a control solution and an input for a drug solution, the minivalve further having a common output for outputting either of the control solution or drug solution to the input of the microdialysis probe; delivering a drug solution and/or control solution to the minivalve; actuating the minivalve between first and second positions in which the control solution or drug solution is selectively input to the microdialysis probe; and detecting the effects of drugs delivered through the microdialysis probe with the use of the microelectrodes.

Also provided are similar systems and methods for delivering one of the drug solution or control solution to an drug ejection device such as a single or multiple cannulas placed at the point of interest in the animal.

BRIEF DESCRIPTION OF THE DRAWINGS

These and other features, aspects, and advantages of the apparatus and methods of the present invention will become better understood with regard to the following description, appended claims, and accompanying drawings where:

FIGS. 9a and 9b illustrate graphical representations of experimental data obtained from a freely behaving rat without having the minivalve on its head and a rat having the minivalve of FIG. 2 mounted on its head, respectively.

DETAILED DESCRIPTION OF THE PREFERRED EMBODIMENT

Although this invention is applicable to numerous and various types of animals, including small animals such as mice and rats and primates including humans, it has been found particularly useful in the environment of small laboratory animals, particularly rats. Additionally, although the minivalve of the present invention can be actuated in many different ways, it has been found particularly effective to use air for actuation. Furthermore, although the solutions from the minivalve can be outputted to either a microdialysis probe or a drug ejection device such as single and multiple cannula(s), it has been found to be more effective to output the solutions to a microdialysis probe. Also, although the minivalve can be mounted on any part of the body, it is preferably mounted on the head. Lastly, the minivalve of the present invention is applicable to the alternate delivery of fluids, such as drugs, whether to an animal or a further apparatus, such as chromathograph. Therefore, without limiting the applicability of the invention to small laboratory rats or animals in general, or to the actuation of the invention with air, or to mounting the invention on the head, or outputting solutions to a microdialysis probe, the minivalve of the present invention will be described in such an environment.

Figure 1:
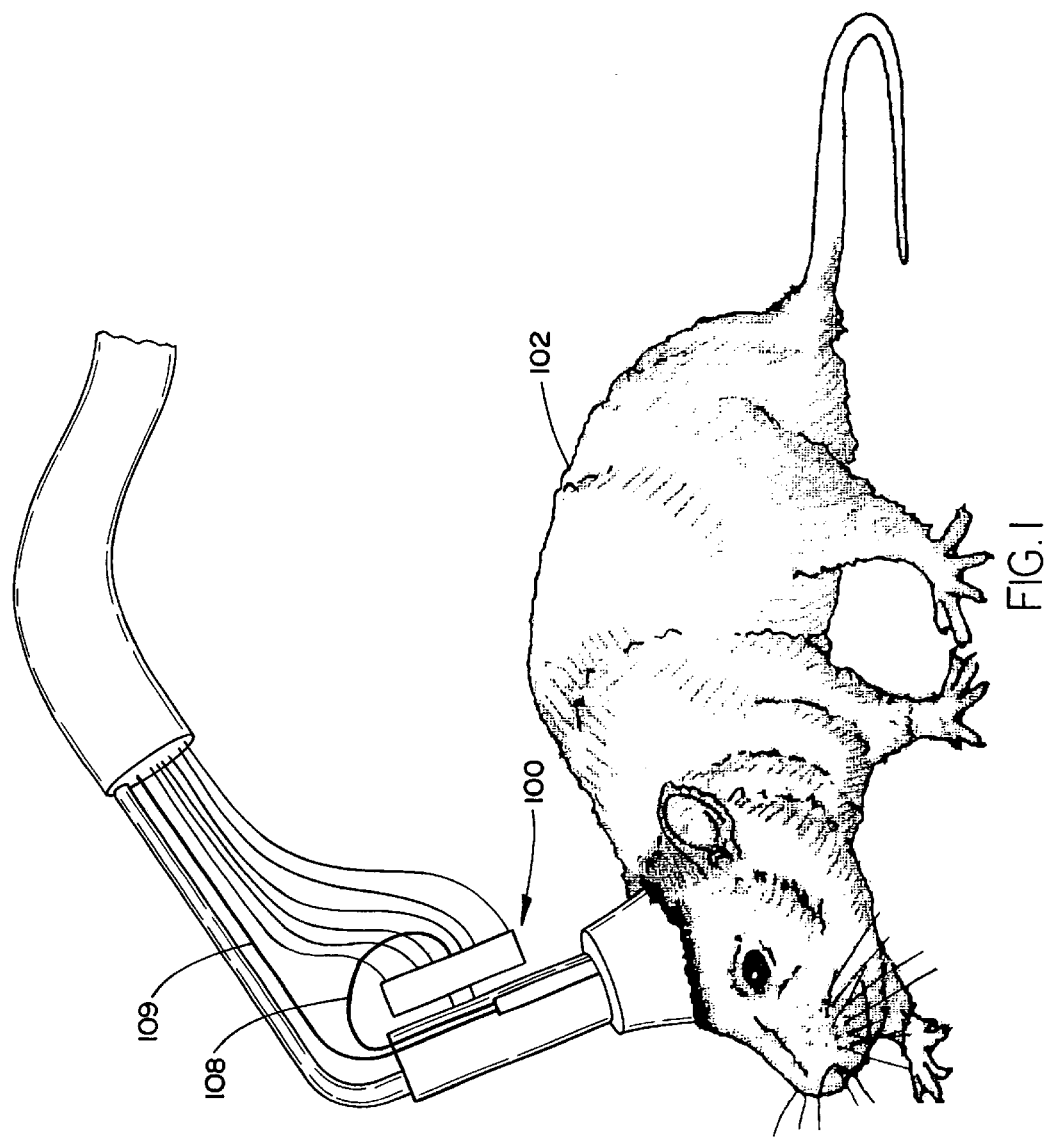
FIG. 1 illustrates the minivalve of the present invention mounted on the head of a laboratory animal.
Figure 2:
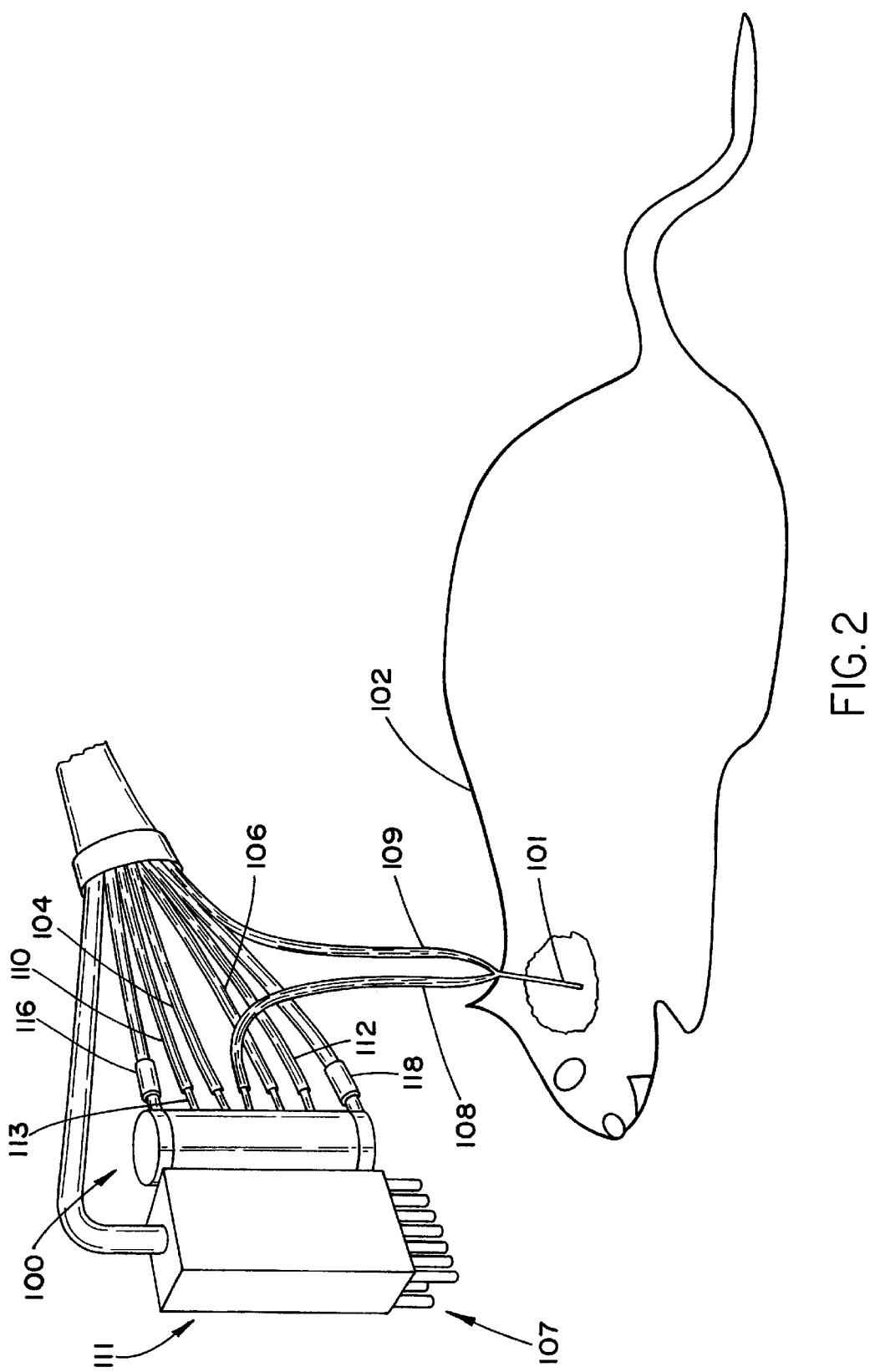
FIG. 2 illustrates a schematical representation of the minivalve of FIG. 1 showing its input and output channels.

Referring now to FIGS. 1 and 2, the minivalve 100 of the present invention is a miniature, lightweight cylindrical liquid switch which can be placed on the head of freely behaving rats 102 or other small animals for drug deliveries into the brain. More specifically, the minivalve 100 is attached to a preamplifier 111 component of a recording cable, bringing the minivalve 100 to as close to the head of the animal as 1 cm. The minivalve 100 of the present invention has been actually reduced to practice having a diameter of approximately 9 millimeters and a length of approximately 27 millimeters resulting in an overall weight of approximately 2 grams.

A novel aspect of the minivalve 100 of the present invention is that it operates with air, which allows its miniaturization, as well as its-functioning without the generation of electrical or acoustic noise. As a consequence, it is ideal for testing drug effects in the brain of freely behaving animals. However, it should be apparent to those in the art that the minivalve can alternatively be actuated with other fluids, such as liquids.

The minivalve 100 of the present invention contains an input channel 104 for a control solution (e.g., ACSF), an input channel 106 for a drug solution, a common fluid output channel 108 to the brain of the animal 102, two waste output channels 110, 112, and a fluid-switch 114 slidably disposed in a main body 115 and moved by microprocessor-regulated air pressure via two air inlet channels 116, 118. The channels are preferably flexible tubing which is force fit over tube stubs 113 integral with the main body 115 of the minivalve 100.

Figure 3A:
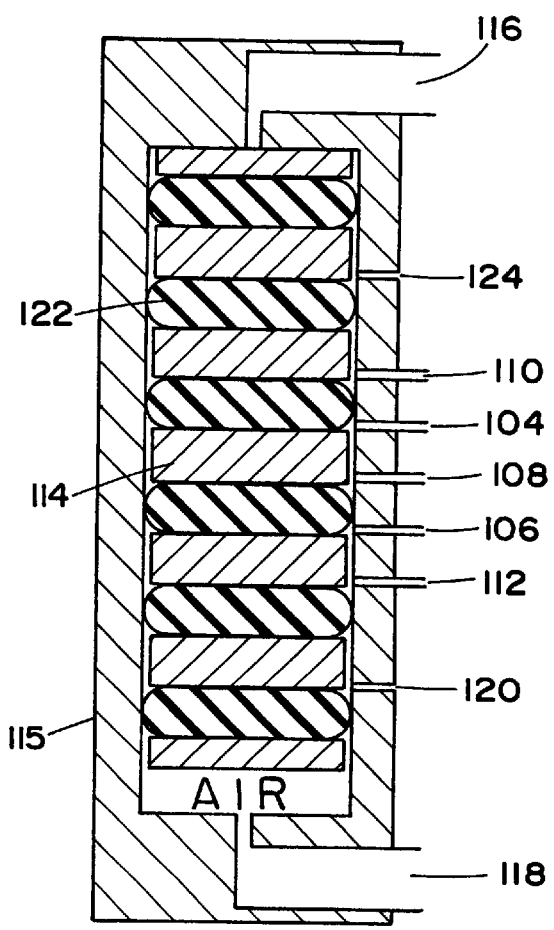
FIGS. 3a and 3b illustrate a first and second position of the minivalve of FIG. 2.
Figure 3B:
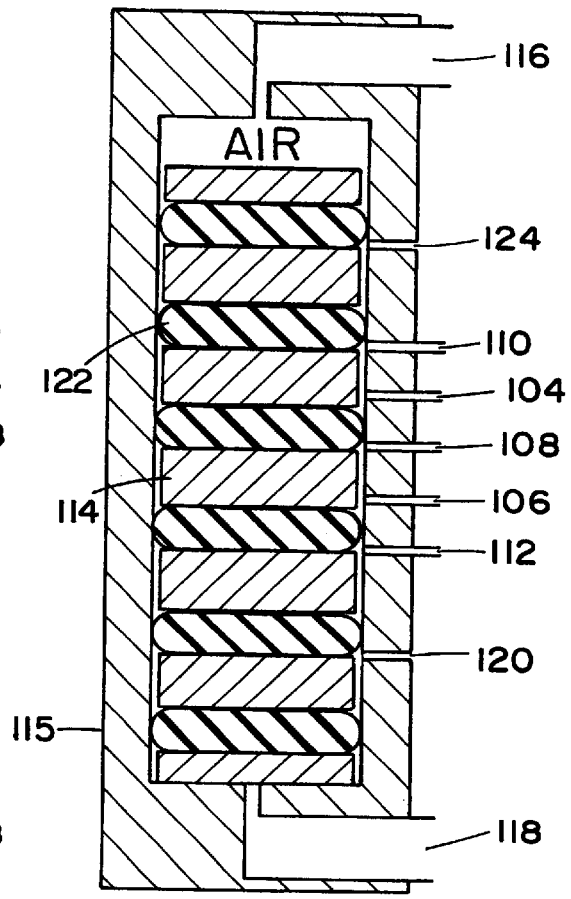

The operation of the minivalve 100 of the present invention is illustrated in FIGS. 3a and 3b. When compressed air is supplied to the air inlet channel 118, the fluid-switch is moved to Position 1 as shown in FIG. 3a. In position 1, the control solution input to the minivalve 100 through input channel 104 flows through the common fluid output channel 108. In this case, the drug solution input into the drug input channel 106 leaves the minivalve 100 via the drug waste channel 112. Thus, while in position 1, the animal 102 receives the control solution via the common fluid output channel 108 of the minivalve 100.

When the compressed air which was introduced into the air inlet channel 118 is vented through a corresponding air escape port 120, and compressed air is introduced into the air inlet channel 116, the fluid-switch inside the minivalve is moved to Position 2, as shown in FIG. 3b. In position 2, the drug solution introduced into the minivalve 100 through the drug input channel 106 flows through the minivalve 100 and leaves through the common fluid output 108. In this case, the control solution introduced into the minivalve through input channel 104 leaves the minivalve 100 via the control waste channel 110. Thus, while in position 2, the animal 102 receives the drug solution via the common fluid output channel 108 of the minivalve 100.

Penetration of the air into the fluid channels is prevented by o-ring seals 122 on the fluid switch 114 and by corresponding air escape ports 120, 124. Thus, the design of the inner structure of the minivalve 100 of the present invention precludes any mixture of the compressed air, the control solution, and the drug solution.

The solution that flows through the common fluid output 108 enters into the inlet of an intracerebrally implanted microdialysis probe or other drug delivery device such as a single or multiple injection cannulas 101. Via this probe/cannula 101, the drug molecules diffuse into a discrete brain area and change the electrical activity of the local neurons. The electrical activity of single neurons, as well as the EEG waves are recorded with extracellular microelectrodes 107, with operational amplifiers (op-amps) 111 serving to eliminate movement artifacts from the recordings. Dialysate from the animal's brain can be collected for testing via tubing channel 109.

These electrophysiological changes are recorded, while the animal is moving freely in a test chamber. The animal's behavior is undisturbed. Indeed, actual testing has shown that its movement pattern is indistinguishable from normal movement patterns.

The minivalve 100 of the present invention is miniature and light enough to be portable by a small animal on its head. In addition, as the device is controlled by air, it causes no acoustic or electrical noise. As a consequence, the minivalve 100 of the present invention enables the experimenter to: (a) deliver drugs into the brain quickly, (b) record the drug-induced effects instantly, and (c) collect artifact-free data.

The small size and light weight of the minivalve 100 allows the device to be carried by a small animals on its head. This allows the alternation of control and drug solutions at a close proximity to the brain, resulting in quick intra-cerebral drug deliveries. In contrast, the currently marketed valves and liquid switches are large and heavy, and therefore cannot be carried by small animals. Furthermore, because the minivalve 100 of the present invention is operated by air, the device does not cause electric or acoustic noise. This allows the collection of artifact-free data from the animal, while the animal's behavior is not disturbed.

Due in part to its small size, the minivalve 100 of the present invention alternates the output of control and drug fluids between two channels. In contrast, the currently marketed large valves can alternate the fluids among many channels. However, this can be compensated by quickly changing the solutions in its channels with the use of high flow rate, multiple syringe pumps (not shown). That is, the minivalve 100 of the present invention can receive different solutions quickly, in a serial fashion.

Figure 4:
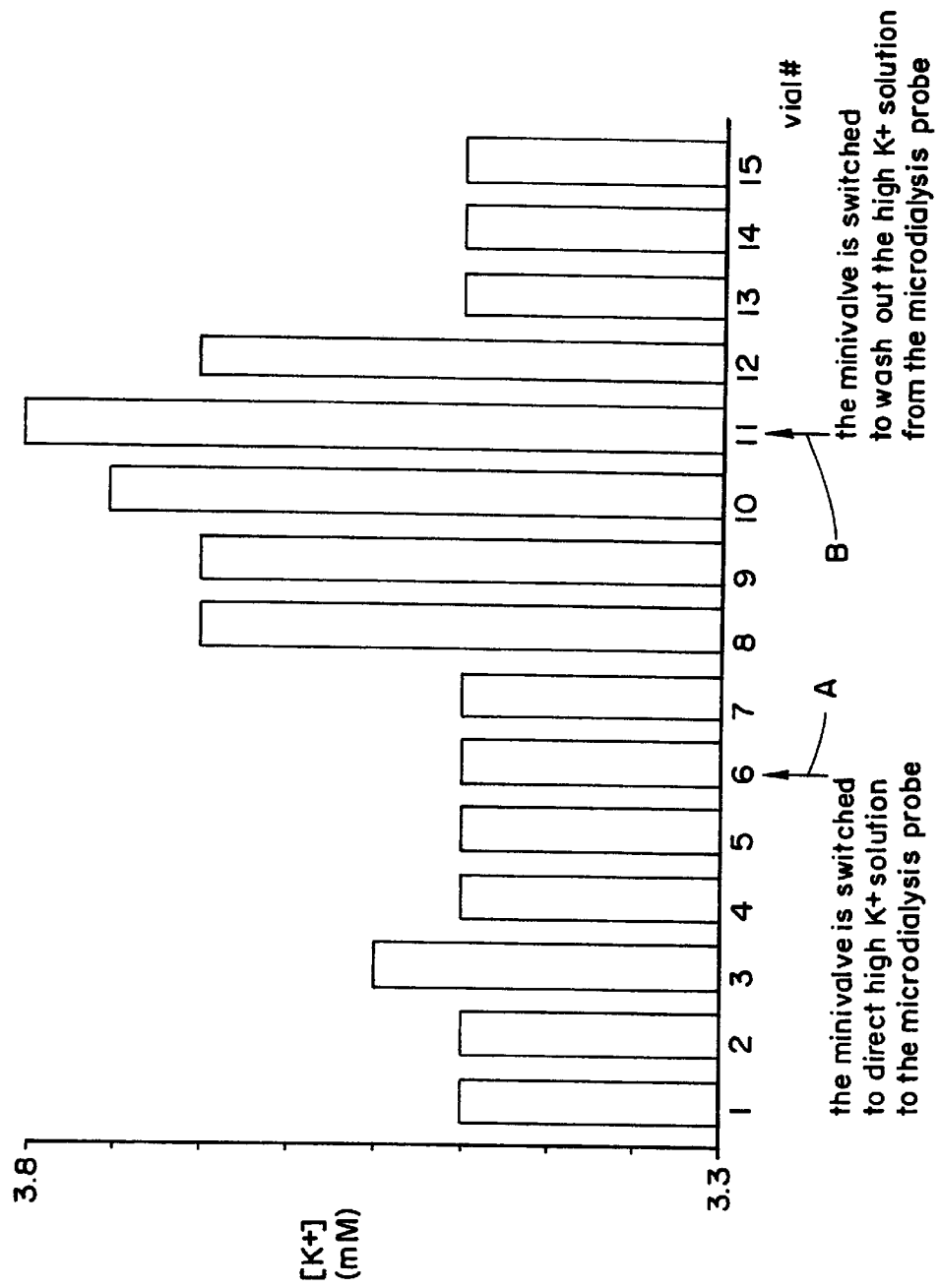
FIG. 4 illustrates a graphical representation of $K^+$ concentrations (mM) in ACSF-containing vials in which a microdialysis probe perfused with excess $K^+$ via the minivalve was immersed, consecutively, for 1 minute intervals.

Referring now to FIG. 4, there is illustrated a graphical representation of $K^+$ concentrations (mM) in ACSF-containing vials in which a microdialysis probe was immersed. The probe was immersed into each vial for 1 min, before, during and after switching the minivalve 100. Switching the minivalve 100 directed a high $K^+$ solution to the tip of the probe for five minutes starting at point A in FIG. 4. The diffusion of excess $K^+$ into the vials occurred two minutes after the switch (from vial 6 to vial 8) and lasted precisely for 5 min (from vial 8 to vial 12). No liquid leakage occurred during this experiment. The $K^+$ solution rapidly reached the microdialysis membrane at the tip of the probe, and elevated the concentration of this ion in the vials. It took no more than two minutes to clear the microdialysis fiber from the excess $K^+$ from the point the minivalve was switched to wash out the high $K^+$ solution from the microdialysis probe at point B to vial 13 where normal levels resumed. It should be apparent to those in the art from FIG. 4, that no mixing of the solutions in the minivalve took place, because increased $K^+$ concentration occurred in the vials only when the minivalve directed the high $K^+$ solution to the microdialysis probe.

Figure 5:
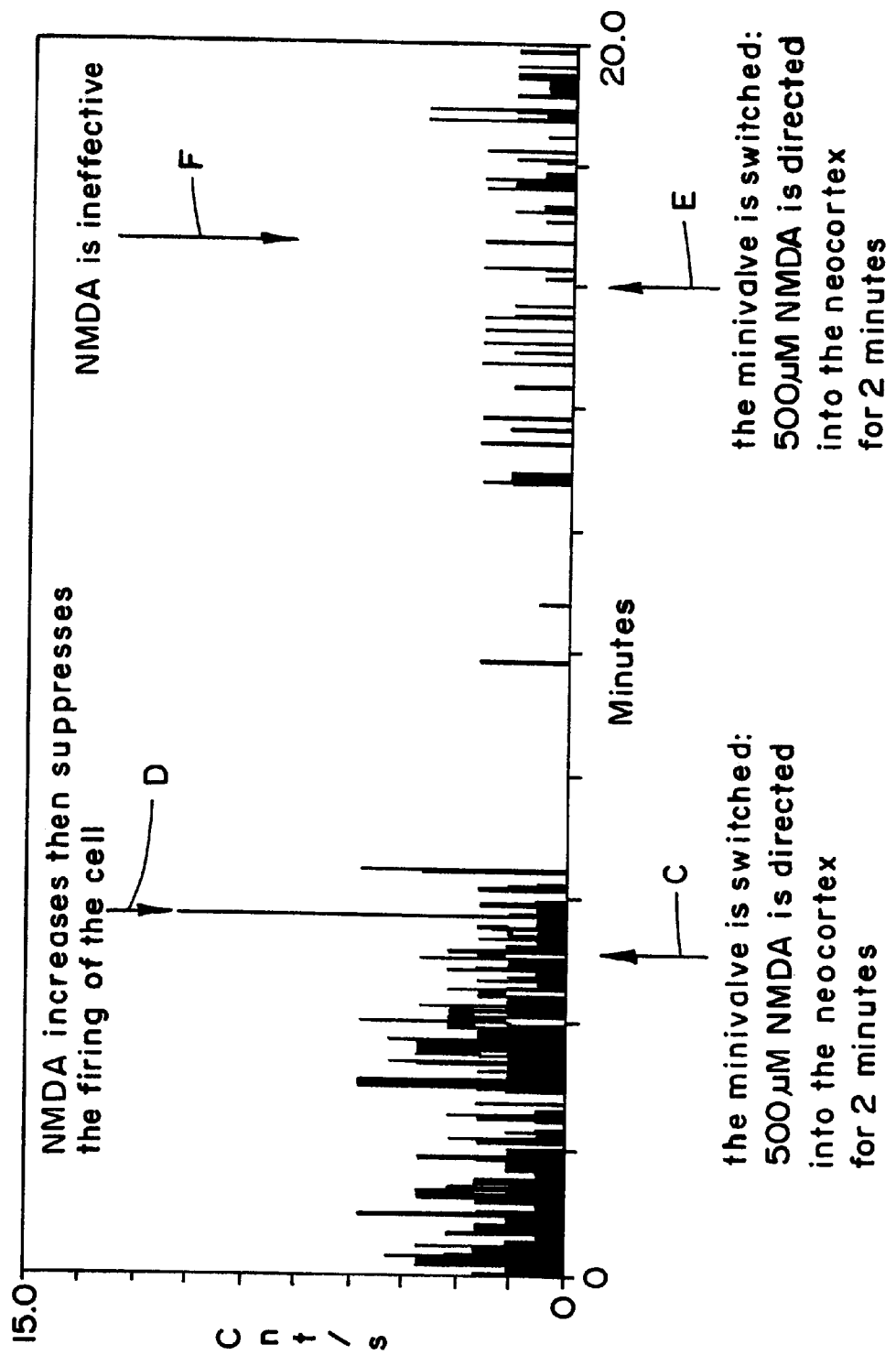
FIG. 5 illustrates a graphical representation of the biphasic effect of NMDA on the firing of a neocortical neuron, and the development of desensitization for this pharmacogical action upon subsequent NMDA exposure for a rat having the minivalve of FIG. 2 mounted on its head.

The biphasic effect of NMDA on the firing of a neocortical neuron, and the development of desensitization for this pharmacogical action upon subsequent NMDA exposure is illustrated in the firing rate histogram of FIG. 5. The experiment was performed on a freely moving rat which carried the minivalve 100 of the present invention on its head as illustrated in FIG. 1.

Within 1 minute after the minivalve switch from position 1 to position 2 at point C, the drug perfusion (500 $\mu$M NMDA) caused a brief firing rate increase at point D, followed by a silent period. Washing out the drug resulted in a recovery of the normal firing pattern of the cell, but the second NMDA delivery at point E was ineffective as shown in area F. This indicates the development of desensitization of NMDA receptors to agonist stimulation. This phenomenon was not due to insufficient drug delivery, because a third NMDA exposure three hours later induced clear excitatory effects associated with an EEG seizure (not shown). This experiment revealed the complex effect of NMDA receptor stimulation on the spontaneous firing of a CNS neuron during behavior. No such data can be obtained in in vitro studies or in anesthetized subjects. Furthermore, the use of the minivalve 100 of the present invention made it possible to detect the NMDA effects quickly within well-defined drug exposure periods. It was not necessary to wait for 20–60 minutes until the drug reached the brain, as in the studies employing traditional valves. This also allowed the use of brief drug delivery periods, since the drug effects could be recognized almost immediately after the minivalve switch. This, in turn allowed the drug delivery to be repeated after a rather short wash-out interval. All of these factors make the experiment using the minivalve of the present invention very economic, providing many pieces of information within a short (20 min) recording session.

Figure 6A:
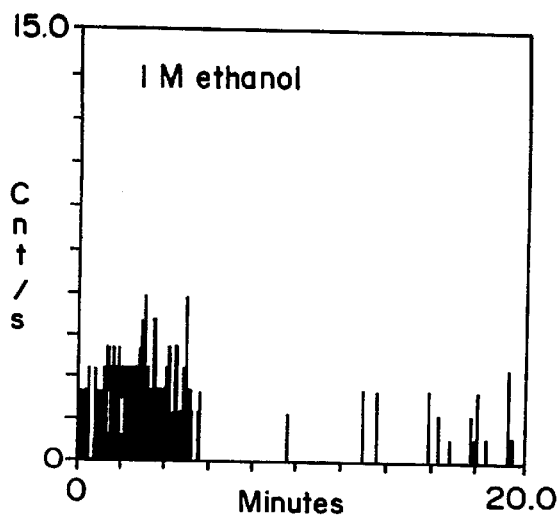
FIGS. 6a–6c illustrate graphical data from a single-cell recording/microdialysis study performed with the minivalve of FIG. 2 for a rat having the minivalve of FIG. 2 mounted on its head.
Figure 6B:
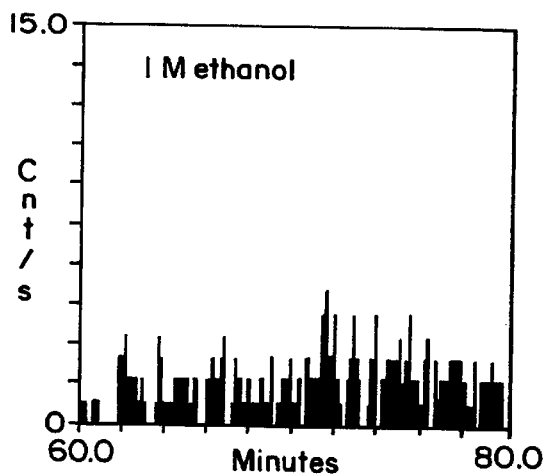
Figure 6C:
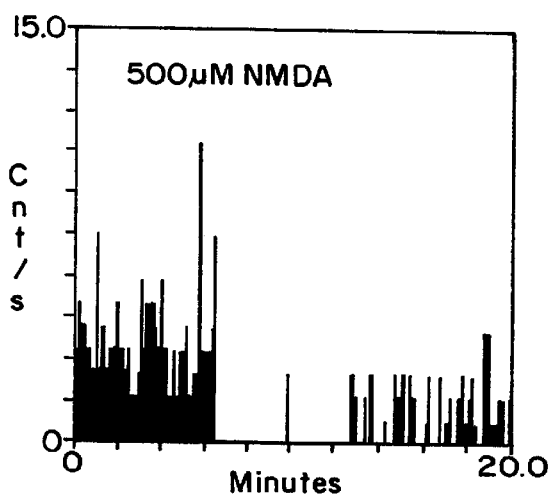

Referring now to FIGS. 6a–6c, there is illustrated graphical data from a single-cell recording/microdialysis study performed with the minivalve 100 of the present invention. The recordings were made from the same single neuron, in the hippocampus of the freely moving rat 102 having the minivalve 100 mounted on its head, as illustrated in FIG. 1. Firing rate histograms for this experiment are shown in FIGS. 6a–6c. Note that a first ethanol perfusion, a histogram for which is illustrated in FIG. 6a, delivered via the minivalve 100 into the hippocampus recording site, suppressed the firing of the recorded neuron as quickly as two minutes after the minivalve 100 activation from position 1 to position 2. However, a second ethanol delivery, a histogram for which is illustrated in FIG. 6b, was ineffective, indicating the development of rapid cellular alcohol tolerance. A subsequent NMDA application through the probe, a histogram for which is illustrated in FIG. 6c, induced an initial firing rate increase, followed by electrical silence. This proved that the inefficacy of the second ethanol perfusion was not due to microdialysis probe dysfunction.

Figure 7:
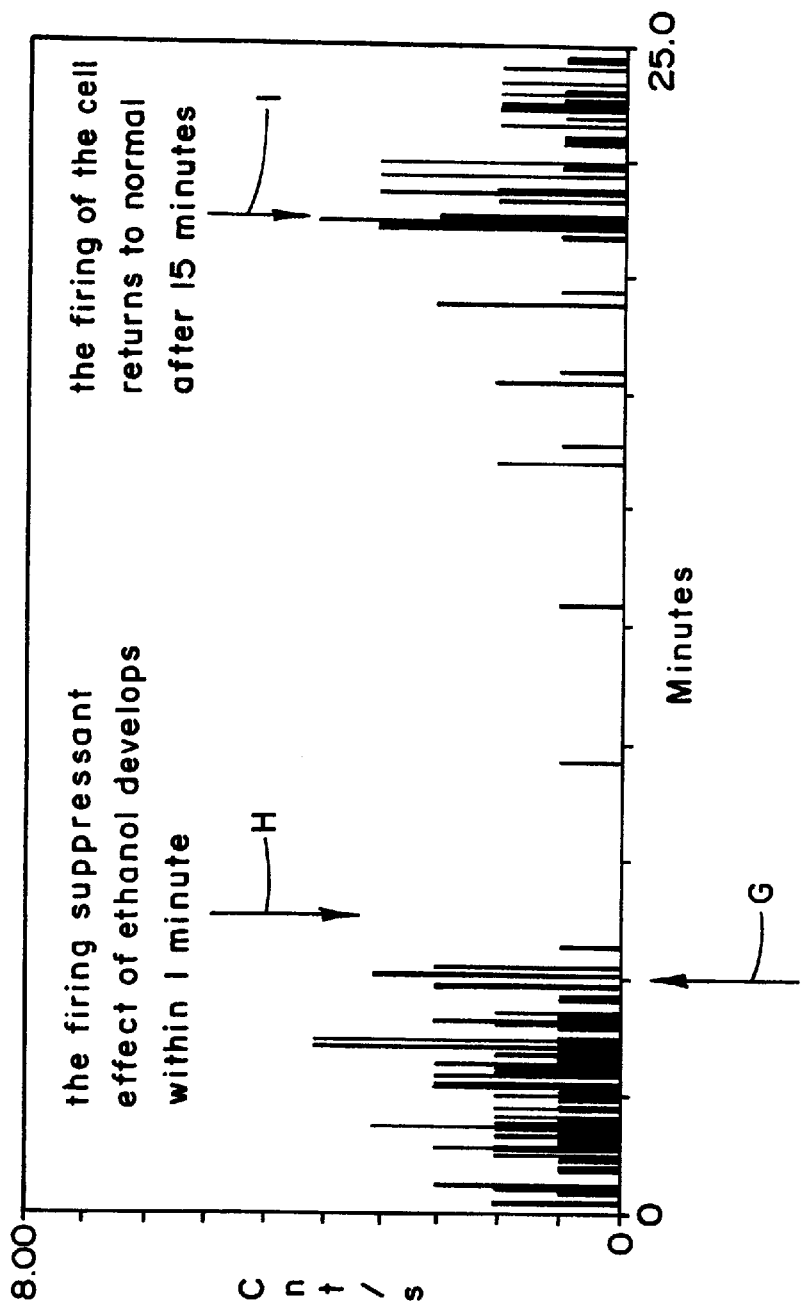
FIG. 7 illustrates a graphical representation of a firing rate histogram showing the instant cell firing suppressant effect of ethanol in the neocortex for a rat having the minivalve of FIG. 2 mounted on its head.

Referring now to FIG. 7, a firing rate histogram is shown illustrating the instant cell firing suppressant effect of ethanol in the neocortex, in a freely moving rat in which the X horizontal axis is time in minutes and the Y axis is the firing frequency in counts per second (Hz). The drug was delivered into the extracellular space of the recorded cell via microdialysis, for two minutes, with the assistance of the minivalve 100 of the present invention at point G. Note that the effect of ethanol develops within one minute after the minivalve was switched to direct the drug into the brain, which is clearly evident at point H. FIG. 7 also demonstrates that when the minivalve 100 of the present invention again directs ACSF into the brain, the normal firing pattern of the cell recovers as shown at point I. Thus, the use of the minivalve 100 of the present invention ensures both rapid drug delivery and rapid wash-out in the brain.

Figure 8:
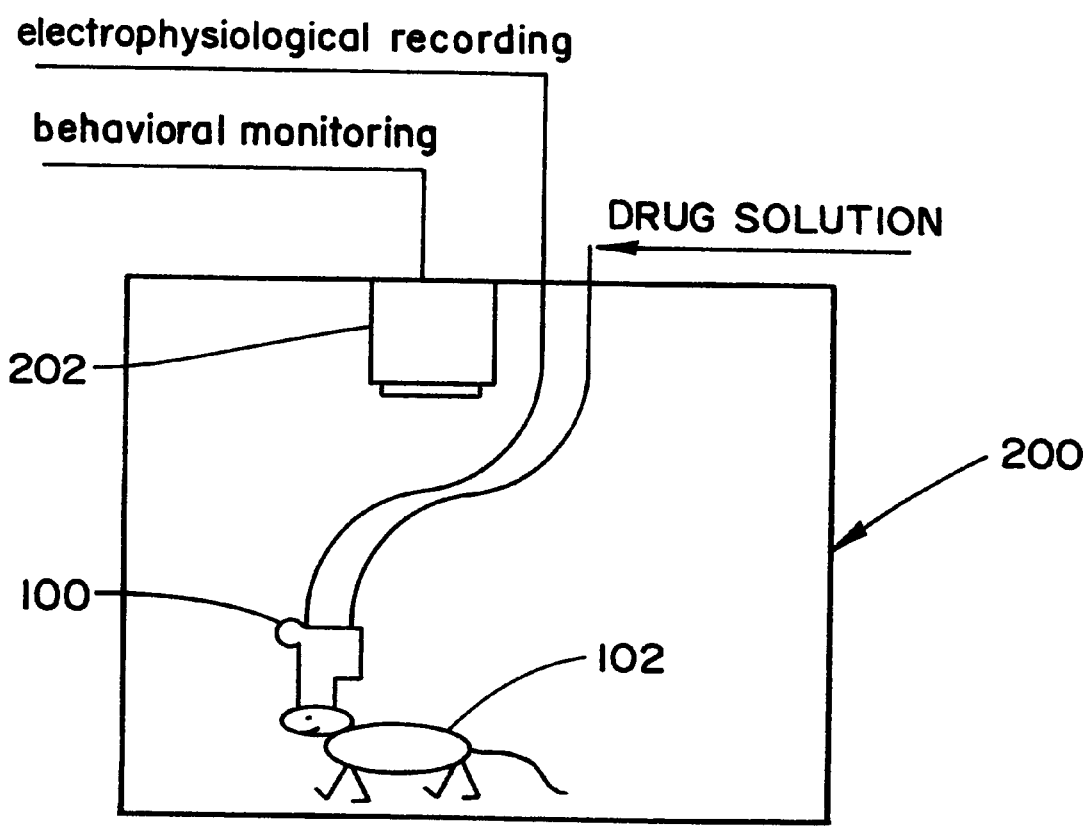
FIG. 8 illustrates an experimental apparatus with a rat having the minivalve of FIG. 2 mounted on its head is under the observance of a camera.

Referring now to FIGS. 8 and 9a–9b, there is demonstrated, the normal movement pattern of a rat 102 carrying the minivalve 100 of the present invention on its head. The data for the map in FIG. 9a was obtained in a rat which did not carry the minivalve 100 of the present invention. The data in FIG. 9b was obtained in an experiment where the minivalve was installed on the head of the rat 102. Both data were collected in 15-min experiment sessions in a cylindrical test chamber 200 illustrated in FIG. 8 in which the subject rat 102 was under the observance of a camera 202. Behavioral data were collected with the use of the camera 202 and a video-tracker system illustrated in FIGS. 9a and 9b. Note that although the two rats preferred different locations in the chamber, the distribution of the pixels in the maps is comparable. Also, the maximal times the rat spent in a pixel-size area is similar in both cases (7.32 sec vs. 7.42 sec). Thus, the rat 102 with the minivalve 100 of the present invention on its head visited every area in the test chamber 200, just like its counterpart, and spent approximately the same time in a given location as the other rat.

Figure 10:
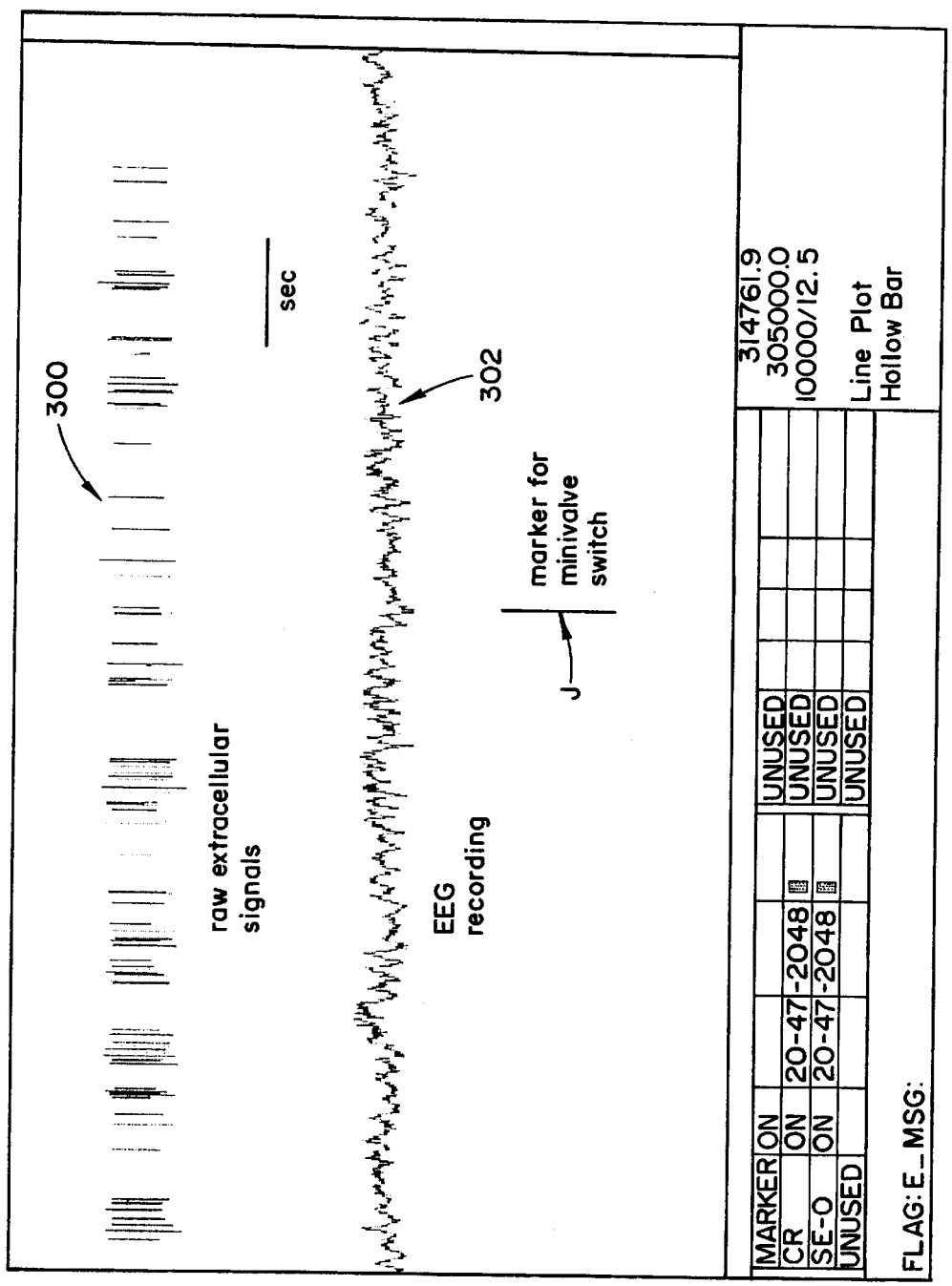
FIG. 10 illustrates a graphical representation of brain electrical activities recorded from a rat having the minivalve of FIG. 2 mounted on its head, the upper trace showing raw extracellular recording data obtained from the hippocampus of the rat, while the lower trace showing the corresponding EEG recording.

Referring now to FIG. 10, there is illustrated experimental evidence illustrating that the use of the minivalve 100 of the present invention does not cause artifacts in electro-physiological recordings. The upper trace 300 of FIG. 10 shows raw extracellular recording data. It was obtained from-the hippocampus of a freely moving rat 102, while the animal was carrying the minivalve 100 of the present invention. The lower trace 302 shows the correspondent EEG recording. Time calibration as indicated. Peak amplitude for the extracellular signals is 250 $\mu$V and for the EEG recording is 500 $\mu$V. The original marker sign, generated during the experimental session, is indicated at point J. Point J indicates the moment the minivalve 100 was switched to drive ethanol to the hippocampal recording site (switched from position 1 to position 2 as illustrated in FIGS. 3a and 3b, respectively). Note the complete lack of artifacts on both recordings. Artifacts were not picked up even during the actual minivalve switch.

The minivalve 100 of the present invention is a miniature, lightweight (approximately 2 g) liquid switch which is portable by small animals on their head. This allows quick drug deliveries into the animal's brain. The operation of the switch from position 1 to position 2 and vice versa is controlled remotely by microprocessor-regulated air pressure. This makes it possible to achieve the drug deliveries without causing acoustic or electric noise. Because of these unique features, the minivalve 100 of the present invention is ideal to rapidly deliver drugs or other materials into the brain and test, instantly, the drug-induced behavioral and/or electro-physiological changes, in natural circumstances, in awake, freely behaving animals (e.g., rats, mice, etc.). Furthermore, the minivalve 100 of the present invention directs either of two continuous fluid streams 104 or 106 into a common output channel 108. This output can be connected to an intracerebrally implanted microdialysis probe 101. Thus, the minivalve is able to deliver drugs into the brain specifically via microdialysis, allowing the experimenter to exploit all the advantages of the powerful microdialysis method.

Because of its novel design the minivalve 100 of the present invention offers a completely new way to determine the effects of drugs (and other compounds) in brain, in natural circumstances, when the animal behaves freely. The rapid intra-cerebral drug deliveries make it possible: (1) to determine drug actions in brain during short, transient behavioral events, (2) to test the primary effects and interactions of a large number of compounds within the same experiment, and (3) to reliably determine the onset and duration of the effects of the delivered drugs.

The minivalve 100 of the present invention can be used for microdialysis/micro-injection experiments to reliably determine the responses of brain cells to various chemical compounds. Thus, the minivalve 100 has applications by neuro-scientists in academia. Furthermore, the minivalve 100 can also be used for economically testing experimental drugs for neurological and psychiatric disorders. Thus, the minivalve 100 of the present invention also has application in the pharmaceutical industry.

Although the minivalve of the present invention is particularly well suited in the area of animal experimentation, it can also be used in a wide range of scientific/industrial pieces of equipment, such as chromatographs, neurochemical analysis systems, and any other device which requires an alternation between fluids.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims. Those modifications may include, but are not restricted to: (1) modifying the minivalve previously described to be activated with liquids instead of compressed gas, (2) modifying the preferred embodiment of the minivalve for its use in animals other than rats, (3) modifying the operation of the minivalve for its use in humans, and (4) modifying the minivalve to be connected to injection cannulas and other fluid ejection devices instead of a microdialysis probe, and (5) modifying the minivalve for its integration into various industrial and scientific instruments.

What is claimed is:

1. A method for delivering through a minivalve one of a control solution or a drug solution to a point of interest in a animal, the method comprising the steps of:

inserting a drug delivery device at a point of interest in the animal, the drug delivery device having an input for acceptance of a solution therein;

mounting a minivalve on the animal, the minivalve having an input for a control solution and an input for a drug solution, the minivalve further having a common output for outputting either of the control solution or drug solution to the input of the drug delivery device;

driving a drug solution and/or control solution to the minivalve; and actuating the minivalve between first and second positions in which the control solution or drug solution is selectively input to the drug delivery device.

2. The method of claim 1, wherein the mounting step comprises mounting the minivalve on the head of the animal.

3. The method of claim 2, wherein the implanting step comprises implanting the drug delivery device in the brain of the animal.

4. The method of claim 1, wherein the drug ejection device is one or more injection cannulas.

* * * * *